United States Patent
Lo

(10) Patent No.: US 6,872,191 B2
(45) Date of Patent: Mar. 29, 2005

(54) SELF-DESTRUCTIVE SYRINGE

(75) Inventor: Pi-Chang Lo, Taoyuan (TW)

(73) Assignee: M.K. Meditech Co., Ltd., Taoyuan (TW)

( * ) Notice: Subject to any disclaimer, the term of this patent is extended or adjusted under 35 U.S.C. 154(b) by 260 days.

(21) Appl. No.: 10/189,444

(22) Filed: Jul. 8, 2002

(65) Prior Publication Data

US 2004/0006308 A1 Jan. 8, 2004

(51) Int. Cl.[7] .............................................. A61M 5/00
(52) U.S. Cl. ..................................... 604/110; 604/228
(58) Field of Search .............................. 604/110, 181, 604/187, 192, 194–195, 197, 218, 221, 228, 239, 240, 243; 128/919

(56) References Cited

U.S. PATENT DOCUMENTS

| | | | | |
|---|---|---|---|---|
| 3,989,044 A | * | 11/1976 | Meierhoefer | 604/192 |
| 4,781,684 A | * | 11/1988 | Trenner | 604/110 |
| 4,932,941 A | * | 6/1990 | Min et al. | 604/110 |
| 5,045,063 A | * | 9/1991 | Spielberg | 604/110 |
| 5,135,495 A | * | 8/1992 | Arcusin | 604/110 |
| 5,531,693 A | * | 7/1996 | Vounatsos | 604/110 |

FOREIGN PATENT DOCUMENTS

EP    1356838 A1 * 10/2003   ............ A61M/5/32

* cited by examiner

Primary Examiner—LoAn H. Thanh
(74) Attorney, Agent, or Firm—Troxell Law Office, PLLC

(57) ABSTRACT

The present invention of a self-destructive syringe includes a hollow needle barrel having a detachable structure disposed between a rubber head and a push rod located therein; a retaining ring is disposed in a proper distance at the front end inside the needle barrel; after the injection, the rubber head of the syringe stays fixedly on the retaining ring; then the push rod is pulled backwardly to separate from the rubber head to form self-destruction; furthermore, connecting tabs are disposed on two opposite areas on a bearing base such that the rod body makes the connecting tabs break via rotation or pulling after the injection thereby causing the rod body to destruct more completely so as to prevent any danger of reusing the syringe.

3 Claims, 7 Drawing Sheets

SELF-DESTRUCTIVE SYRINGE

BACKGROUND OF THE INVENTION

1) Field of the Invention

The present invention relates to a self-destructive syringe, more especially to a syringe having a design of a detachable structure disposed between a push rod structure and a rubber head, furthermore, a retaining ring is disposed at the front rim inside the syringe; wherein, after being pushed forwardly for injection, the rubber head is clamped by the retaining ring to detach from the push rod for self-destruction.

Another embodiment of the present invention of a self-destructive syringe has connecting tabs disposed on two opposite areas on a bearing base; the thinness of the material of the connecting tabs allowing the rod body to make the connecting tab break via rotation or pulling after injection thereby destructing the rod body more completely so as to prevent the repetitive use of the syringe.

2) Description of the Prior Art

The issues of medically related contamination should not be neglected since many terminal diseases are infected through the blood. It is very important to require sole or personal use of the medical instruments. The present invention of a self-destructive syringe is designed to meet that requirement.

Since it directly contacts with the patient's body, the injection syringe should be discarded right after application and not be used again onto another patient's body. However, some medical units only throw away the needle head portions but reuse the needle barrel portions. That is very dangerous because although the needle barrel portions do not touch the patient directly, the blood probably refluxes and carries the bacteria or virus into the needle barrel. It is very possible that the next patient injected by the syringe with the same needle barrel would be contaminated through the bacteria or virus mixed inside the medicine. That not only deprives the patient's rights and interests, but also endangers his or her life.

SUMMARY OF THE INVENTION

The primary objective of the present invention of a self-destructive syringe designed to provide a syringe structure not able to be reused mainly comprises a needle barrel having a detachable structure disposed between a rubber head and a push rod located therein; a retaining ring is disposed in a proper distance at the front end inside the needle barrel; after the injection, the rubber head of the syringe stays fixedly on the retaining ring; then the push rod is pulled backwardly to separate from the rubber head such that the syringe is not able to be used again for sucking medicine thereby becoming self-destructive so as to prevent any danger of reusing the syringe.

Another embodiment of the present invention is to dispose connecting tabs on two opposite areas of a bearing base such that the rod body breaks the connecting tabs via rotation or pulling after the injection thereby destructing the rod body more completely so as to prevent any danger of reusing the syringe.

To enable a further understanding of the structural features and the technical contents of the present invention, the brief description of the drawings below is followed by the detailed description of the preferred embodiment.

DETAILED DESCRIPTION OF THE PREFERRED EMBODIMENTS

Figure 1:
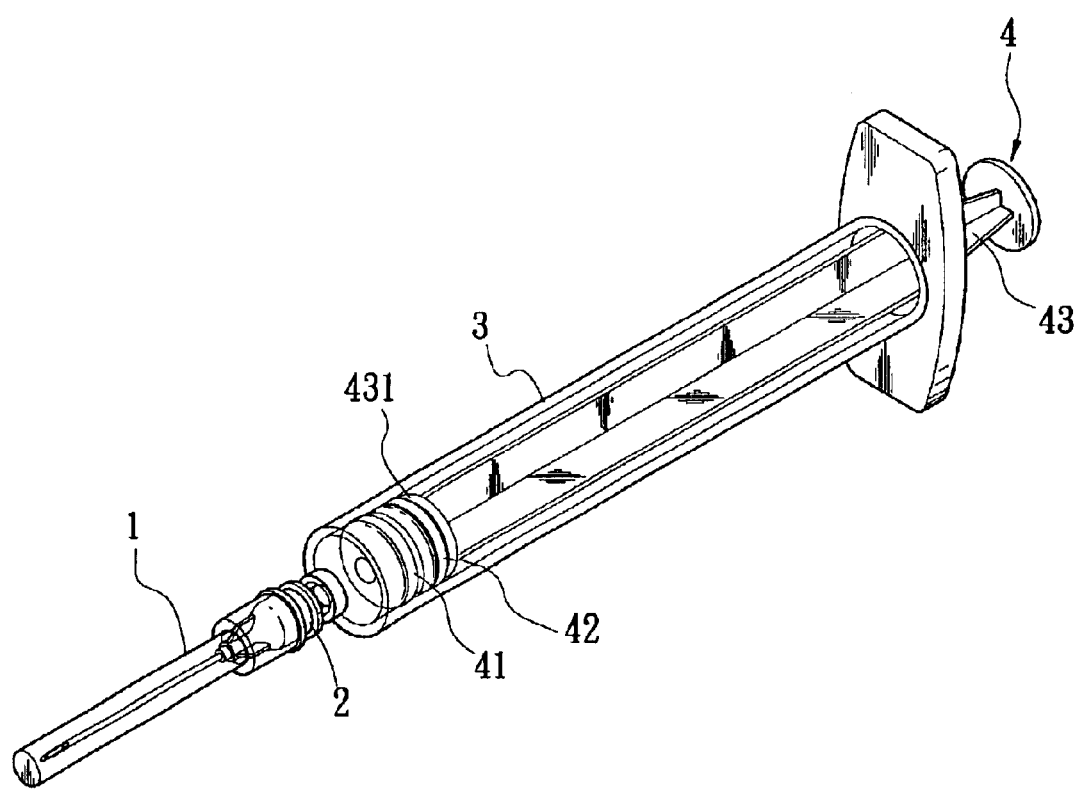
FIG. 1 is a pictorial and schematic drawing of the assembly of the present invention.
Figure 2:
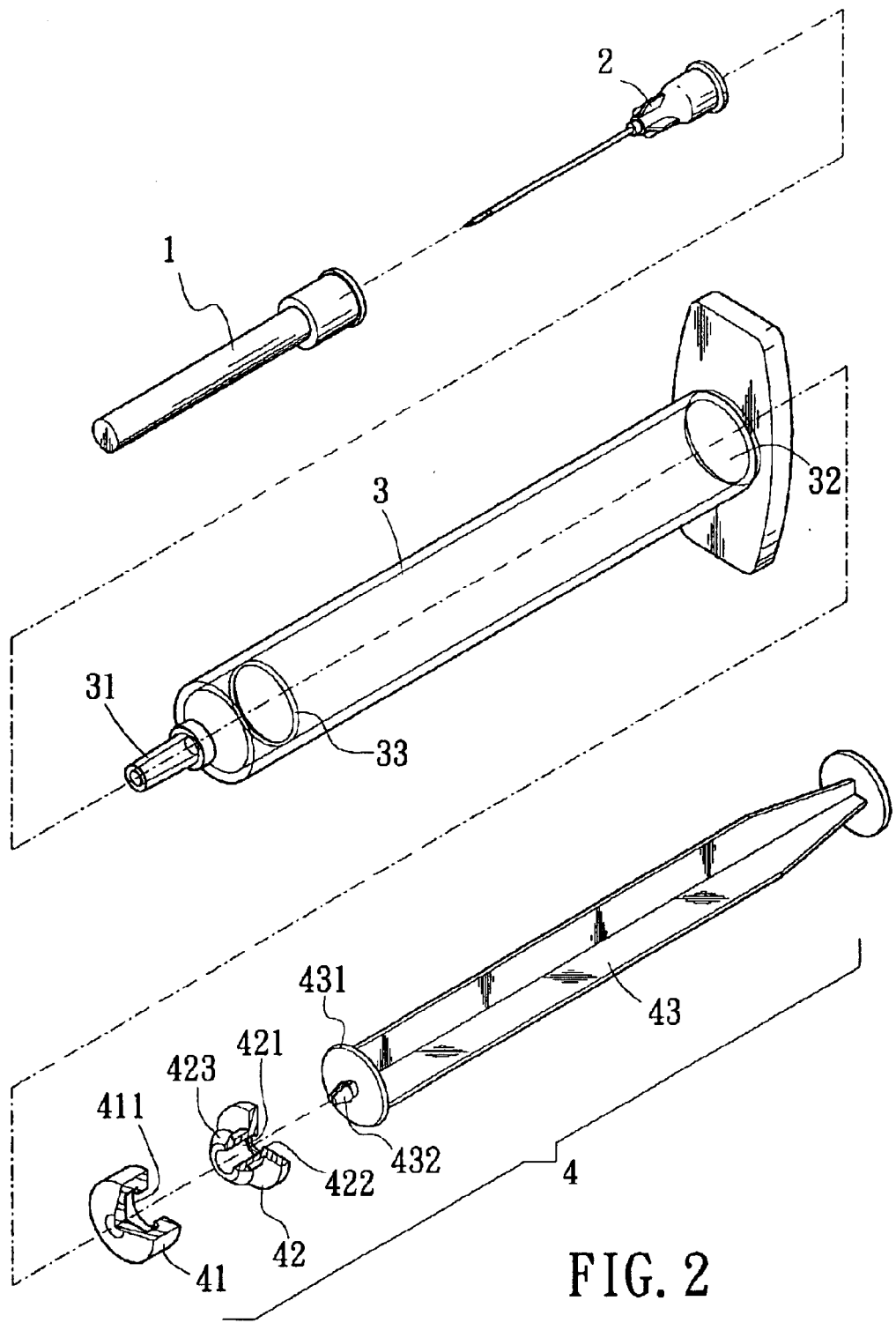
FIG. 2 is a pictorial, exploded and schematic drawing of the structure of the present invention.
Figure 3:
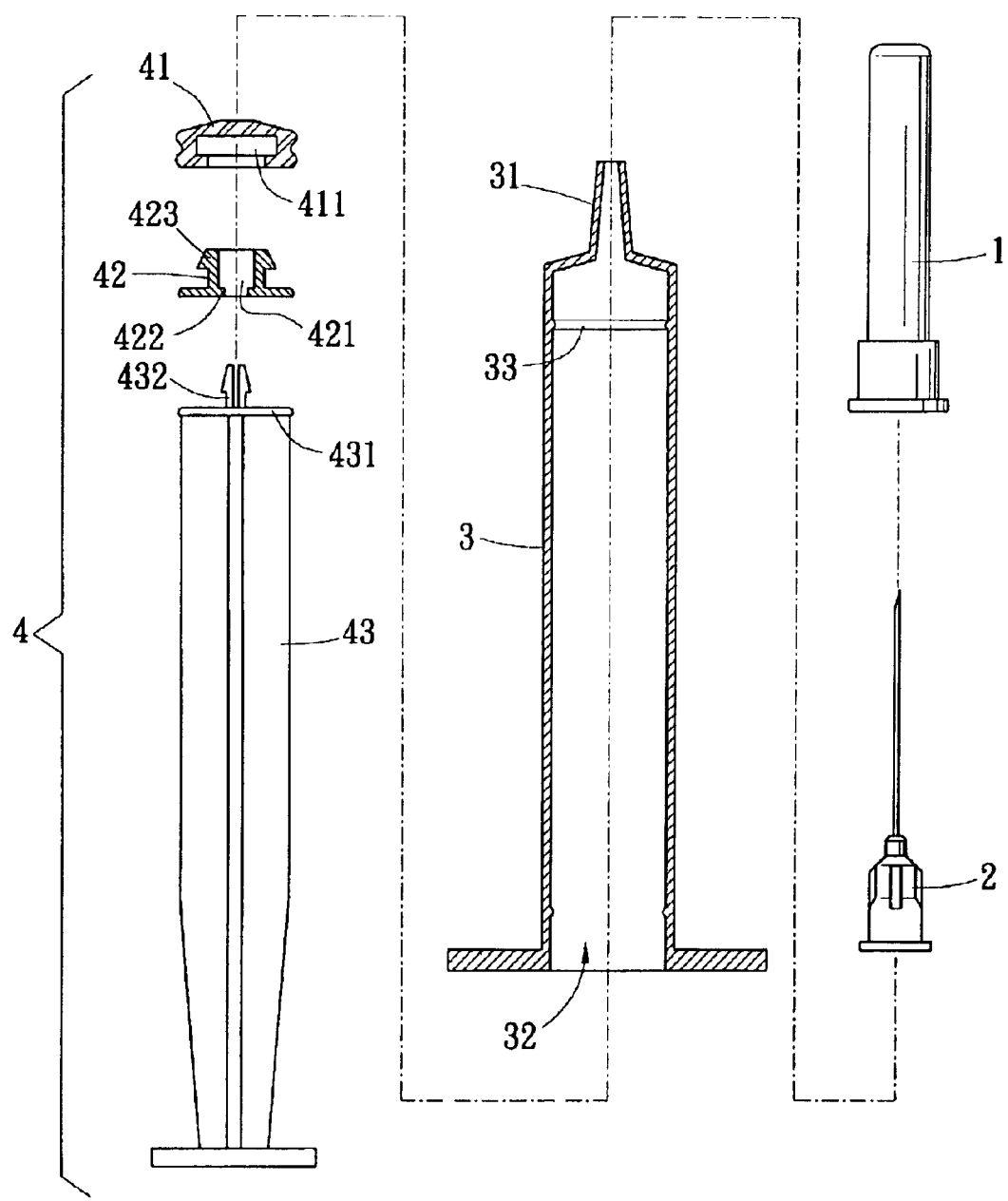
FIG. 3 is a planar, exploded and schematic drawing of the present invention.
Figure 4A:
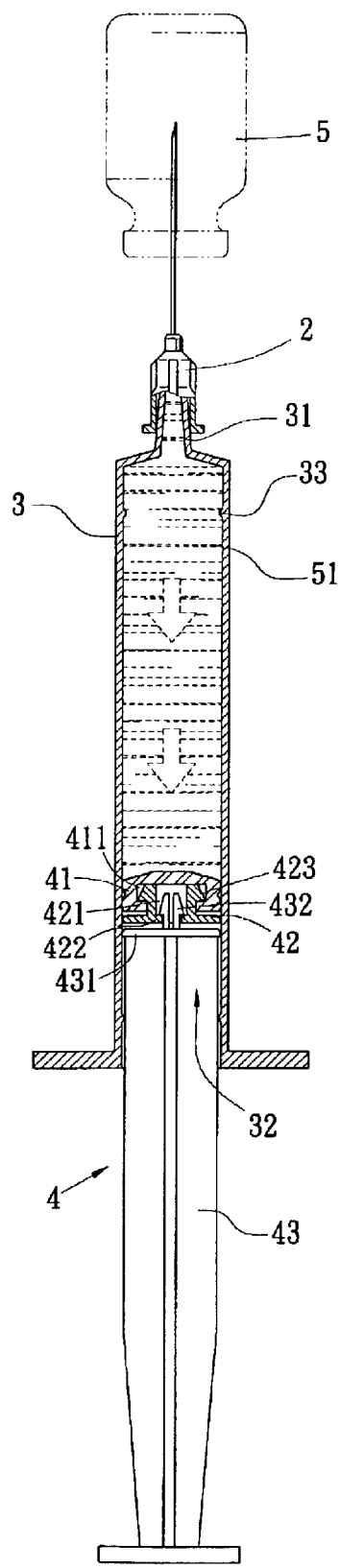
FIG. 4A is the first schematic drawing of the application of the present invention.
Figure 4B:
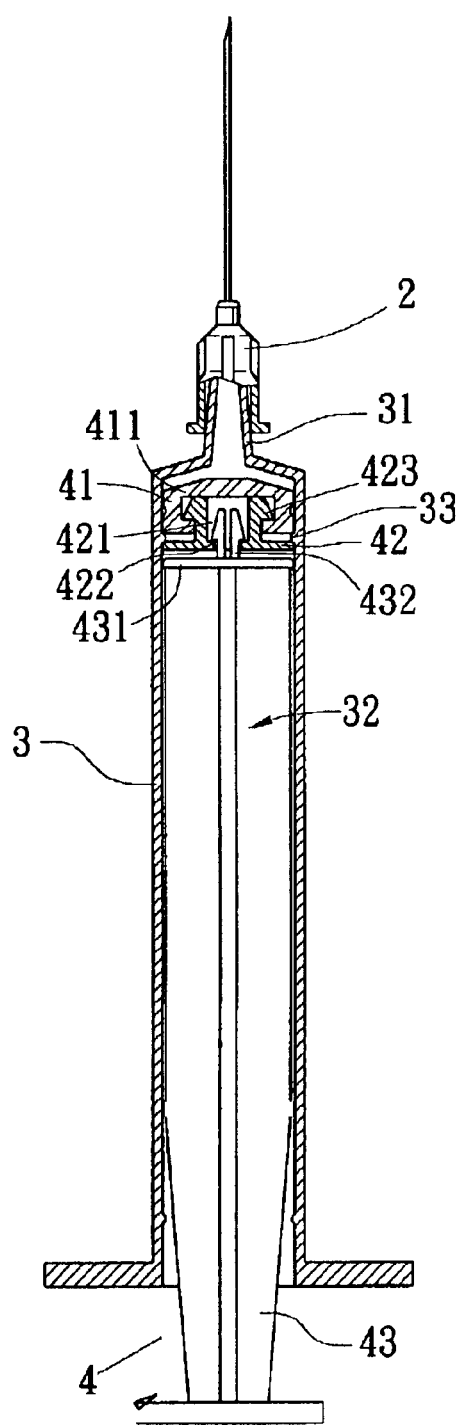
FIG. 4B is the second schematic drawing of the application of the present invention.
Figure 4C:
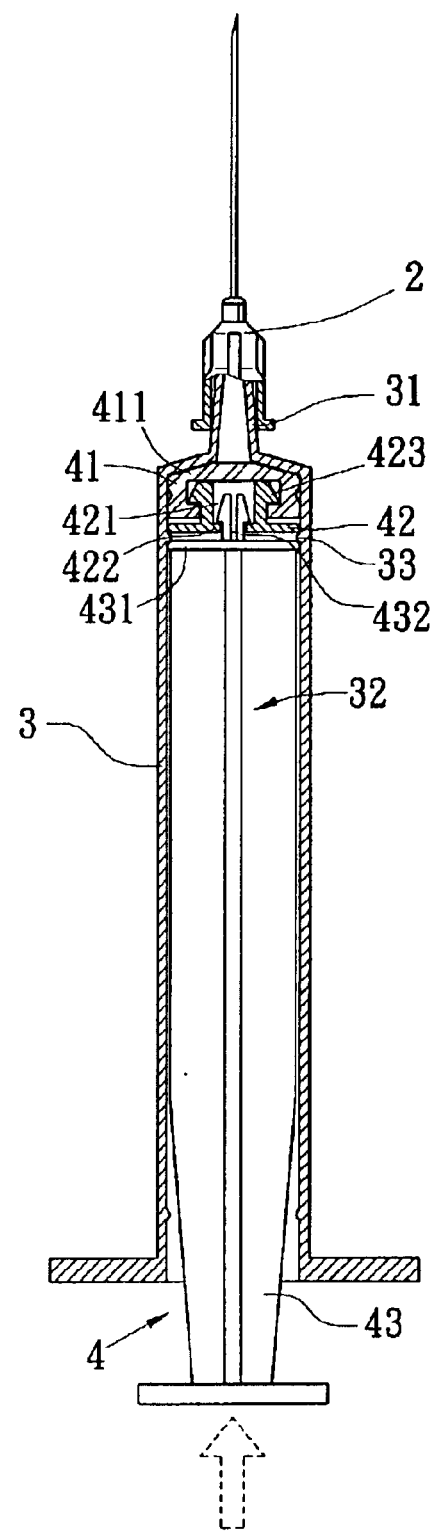
FIG. 4C is the third schematic drawing of the application of the present invention.
Figure 4D:
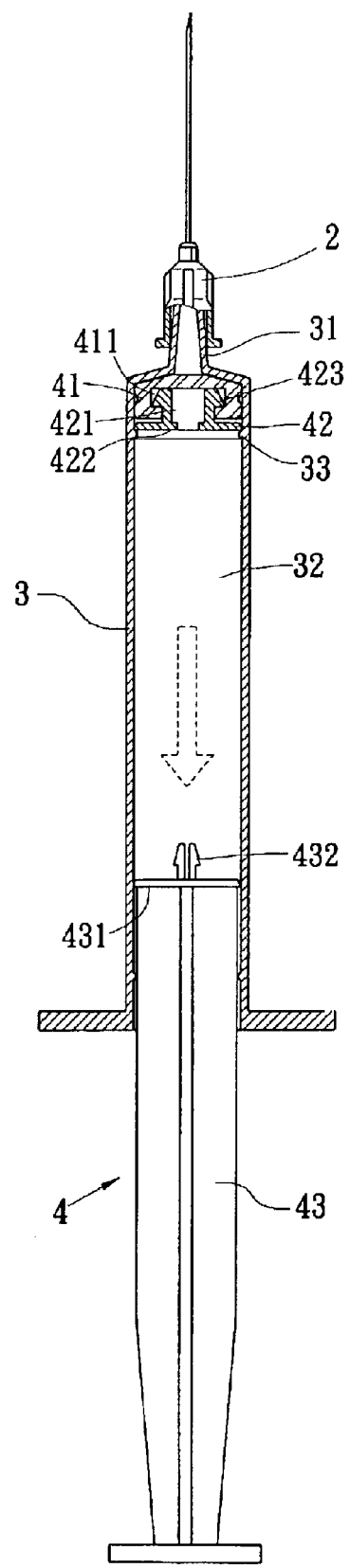
FIG. 4D is the fourth schematic drawing of the application of the present invention.

FIGS. 1, 2 and 3 show the pictorial, assembled, planar, exploded and schematic drawings of the present invention; as indicated, the present invention of a self-destructive syringe mainly comprises a needle case (1), a needle base (2), a hollow needle barrel (3) and a push rod (4), wherein the structure of the push rod (4) includes a rubber head (41), a bearing base (42) and a rod body (43); the front end of the hollow needle barrel (3) is disposed with an adapter (31) for connecting the needle base (2); the needle case (1) cases the needle base (2) for storage; the receiving slot (32) of the needle barrel (3) receives the push rod structure (4) so as to form a complete injection syringe.

The main structural design thereof has a retaining ring (33) disposed in a proper distance from the front end of the receiving slot (32) of the needle barrel (3); that proper distance fits between the interval distance for assembling the rubber head (41) and the bearing base (42); the push rod (43) structure has a base portion (431) formed at the front end thereof; a retaining portion (432) is disposed at the center of the base portion (431) corresponding to a retaining slot (421) fixedly connected with the bearing base (42); the retaining slot (421) has a step ring (422) provided for inserting the retaining portion (432); furthermore, a clamp portion (423) is formed on the bearing base (42) to connect with a hollow portion (411) of the rubber head (41) so as to accomplish the assembly of the entire push rod structure (4).

FIGS. 4A to 4D show the schematic drawing of the application t of the present invention; as indicated, when a medical worker uses the present invention, the operation steps involved are exactly the same as that of using a conventional injection syringe; first, the needle base (2) inserts into a medicine bottle (5) filled with injection medicine and the rod body (43) pulls back to suck the medicine fluid (51). The circumferential rim of the rubber head (41) of the push rod structure (4) and the receiving slot (32) of the hollow needle barrel (1) form air-tight vacuum thereby allowing the rubber head (41) to make pistol movement in the receiving slot (32) so as to suck the medicine fluid (51) to the hollow needle barrel (1) from the medicine bottle (5) for injection.

During injection, the rod body (43) is again pushed to inject the medicine fluid (51) into the patient's body through the air-tightness formed by the rubber head (41); when the rubber head (41) is pushed against the retaining ring (33) at the front end of the hollow needle barrel (1), the injection movement is accomplished and at this time, the medical worker extracts the needle base (2) out of the patient.

To eliminate the reuse of the hollow needle barrel (1), the user once again pushes the rod body (43) when the rubber head (41) presses against the retaining ring (33) to place the rubber head (41) and the bearing base (42) completely into the front end of the retaining ring (33) for retaining purpose; at this time, the medical worker extracts the rod body (41) again to make the retaining portion (432) of the base portion (431) separate from the step ring (422) of the retaining slot (421) of the bearing base (42); since the retaining force of the retaining ring (33) is greater than that of the retaining portion (432) applied onto the step ring (422), to pull the rod body (41) back makes the rubber head (41) and the bearing base (42) fix at the front end of the retaining ring (33) completely to further form self-destruction so as to prevent the improper recycle of the hollow needle barrel (1) to be reused for the second time. Therefore, anyone trying to reuse the hollow needle barrel (1) of the present invention will find that pulling or pushing the rod body (41) is not able to control the rubber head (41) to make piston sucking movement in the receiving slot (32); in addition, the rubber head (41) and the bearing base (42) are completely retained by the retaining ring (33); the rubber head (41) and the bearing base (42) can't be withdrawn from the retaining ring (33) at all thereby preventing the repetitive use of the hollow needle barrel (1) and eliminating any possible contamination.

Figures 5A, 5B:
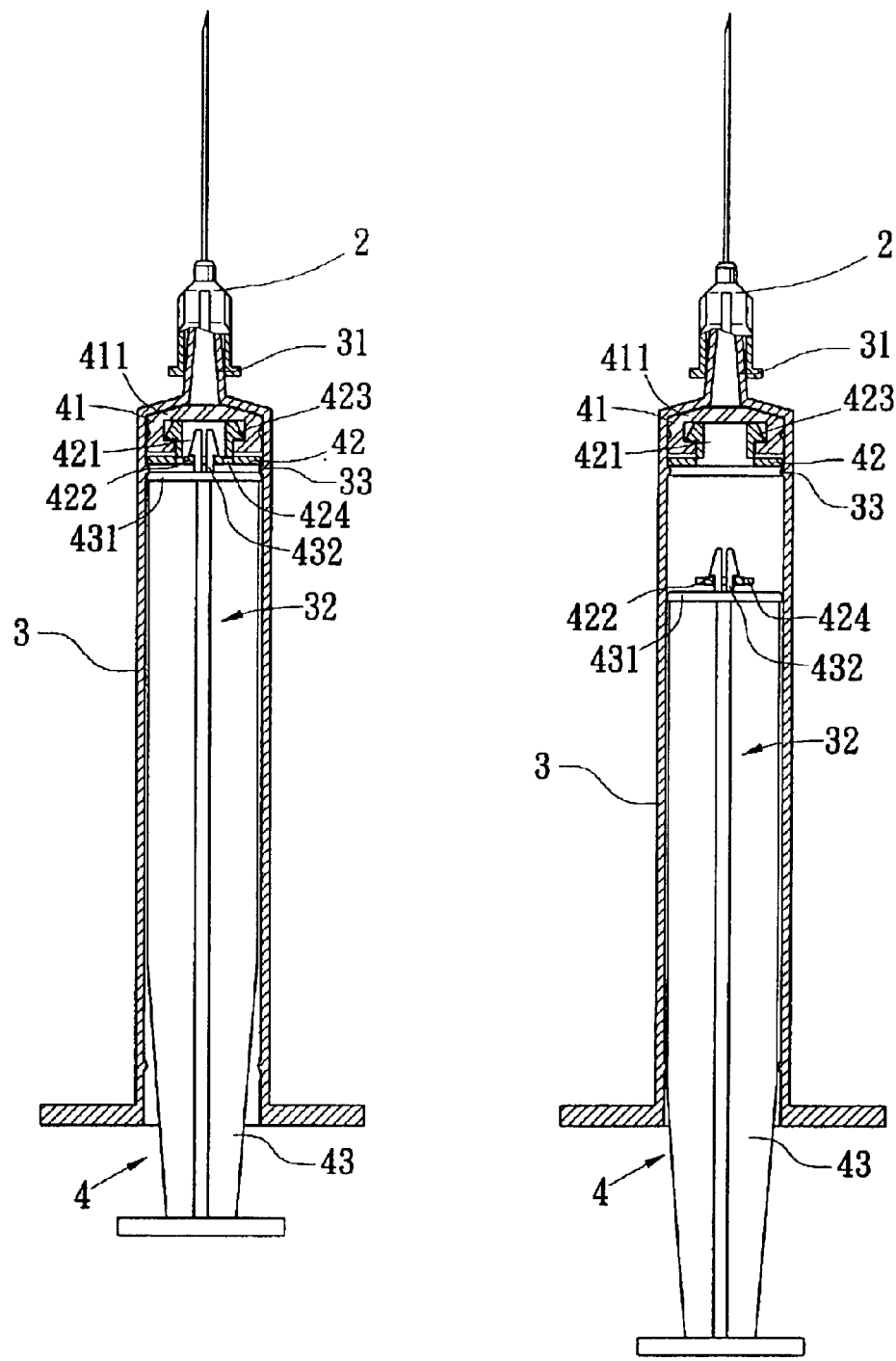
FIG. 5A is a schematic drawing of another exemplary embodiment of the present invention.
FIG. 5B is a drawing of the action of another exemplary embodiment of the present invention.

FIGS. 5A and 5B show another embodiment of the present invention; as indicated, the push rod structure (4) of the present invention has connecting tabs (424) disposed on two opposite areas of the step ring (422) of the bearing base (42); after injection, through the abovementioned action, when the rubber head (41) and the bearing base (42) drop into the retaining ring (33), to rotate or pull the rod body (43) breaks the connecting tabs (424) thereby completely separating the rod body (43), the rubber head (41) and the bearing base (42) so as to form a thorough destruction and absolutely eliminate the danger of reusing the syringe.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. A self-destructive syringe comprising:
   a) a hollow needle barrel having:
      i) an adaptor located on a first end;
      ii) a retaining ring located on an interior thereof; and
      iii) a receiving slot located between the retaining ring and the adaptor;
   b) a needle base inserted on the adaptor;
   c) a needle case inserted on the needle base; and
   d) a push rod having:
      i) a rubber head slidably inserted into the hollow needle barrel and having a hollow portion;
      ii) a bearing base having a clamping portion, a retaining slot and a step ring, the clamping portion of the bearing base being inserted into the hollow portion of the rubber head; and
      iii) a rod body having a retaining portion on a base portion moveable between connected and disconnected positions,
   wherein, when the retaining portion relative to this rubber head is in the connection position, the retaining portion is inserted into the retaining slot and engaging the step ring of the bearing base, and the rubber head and the bearing base are located in the hollow needle barrel between the retaining ring and a second end of the hollow needle barrel, and when the retaining portion is in the disconnected position, the retaining portion of the rod body is separated from the bearing base, and the rubber head and the bearing base are locked in the receiving slot by the retaining ring.

2. The self-destructive syringe according to claim 1, wherein the retaining portion of the rod body is removably connected to the step ring of the bearing base.

3. The self-destructive syringe according to claim 1, wherein the step ring includes a connecting tab that breaks away from step ring when the retaining portion is in the disconnected position, the retaining portion of the rod body is connected to the connecting tab of the step ring of the bearing base.

* * * * *